United States Patent
Campbell et al.

(10) Patent No.: US 6,207,878 B1
(45) Date of Patent: Mar. 27, 2001

(54) SARCOSPAN-DEFICIENT MOUSE AS A MODEL FOR CLINICAL DISORDERS ASSOCIATED WITH SARCOSPAN MUTATIONS

(75) Inventors: Kevin P. Campbell; Connie Lebakken; Rachelle Crosbie; Roger Williamson, all of Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/422,762

(22) Filed: Oct. 21, 1999

(51) Int. Cl.⁷ .................. A01K 67/027; G01N 33/00
(52) U.S. Cl. .................... 800/18; 800/18; 800/3
(58) Field of Search .................. 800/8, 3, 9, 18, 800/21

(56) References Cited

PUBLICATIONS

Brown RH. Annu Rev Med 48:457–466, 1997.*
Shastry BS. Molecular and Cellular Biochemistry 181:163–179, 1998.*
Lebakken et al. Mol. Cell. Biol. 20, 1669–1677, 2000 (abstract).*
Huetz F. Eur. J. Immunol.27: 307–314, 1997.*
Heighway et al., *Genomics 35*: 207–214 (1996).
Maecker et al., *Faseb 11*: 428–442 (1997).
Crosbie et al., *J. Biol. Chem. 272*: 31221–31224 (1997).
Crosbie et al., *J. Cell Biol. 145* : 153–165 (1999).

* cited by examiner

*Primary Examiner*—Scott D. Priebe
*Assistant Examiner*—Ram R. Shukla
(74) *Attorney, Agent, or Firm*—Kevin M. Farrell

(57) ABSTRACT

Disclosed is a transgenic knockout mouse whose genome has a homozygous disruption in its endogenous sarcospan gene, wherein the disruption prevents the synthesis of functional sarcospan in cells of the mouse. The mouse is characterized as exhibiting from 1.4 to 6.8 fold larger epididymal fat pad deposits as compared to the epididymal fat pad deposits of a wild type mouse. Methods for production of the mouse are presented. Also disclosed are cells derived from the transgenic knockout mouse. The mouse can be used in a method for identifying therapeutic agents for the treatment of an individual diagnosed with a metabolic disorder associated with a reduction or loss of expression of wild-type sarcospan. An example of such a disorder is weight gain in the individual associated with a reduction or loss of expression of wild-type sarcospan. These specific methods are also provided.

11 Claims, 4 Drawing Sheets

SARCOSPAN-DEFICIENT MOUSE AS A MODEL FOR CLINICAL DISORDERS ASSOCIATED WITH SARCOSPAN MUTATIONS

BACKGROUND OF THE INVENTION

The dystrophin-glycoprotein complex (DGC) is a multi-subunit protein complex expressed at the sarcolemma of skeletal, cardiac, and smooth muscle fibers (reviewed in Campbell, Cell 80: 675–679 (1995), and Straub and Campbell, Curr. Opin. Neurol. 10: 169–175 (1997)). The DGC is currently known to be composed of at least nine proteins including dystrophin, the syntrophins, α- and β-dystroglycan, α-, β-, γ-, and δ-sarcoglycans and sarcospan. One of the functions of the DGC is likely to provide a structural link between the extracellular matrix and the actin cytoskeleton through interactions of dystrophin with filamentous actin, and α-dystroglycan with the extracellular matrix component laminin, thereby maintaining the stability of the sarcolemma under contractile forces (Ervasti and Campbell, J. Cell Biol. 122(4): 809–823 (1993); and Campbell, Cell 80: 675–679 (1995). Recent evidence suggests that the DGC may play other roles in normal muscle physiology through interactions with cell signaling molecules or other proteins at the sarcolemma.

Sarcospan is the most recently cloned component of the DGC (Crosbie et al., J. Biol. Chem. 272: 31221–31224 (1997). Hydropathy plots predict that the protein has four transmembrane domains with an extracellular loop extending between transmembrane domains 3 and 4 (Scott et al., Genomics 20: 227–230 (1994); Crosbie et al., J. Biol. Chem. 272: 31221–31224 (1997). Dendogram analysis designates sarcospan as a member of the tetraspan superfamily, also known as the transmembrane-4 superfamily or the tetraspanins (Heighway et al., Genomics 35: 227–230 (1996); Wright and Tomlinson, Immunol. Today 15: 588–594 (1994). Tetraspan proteins are thought to function as molecular facilitators, mediating interaction between proteins at the plasma membrane. The tetraspans have also been implicated in cell adhesion, migration, and proliferation (Wright et al., Immunol. Today 15: 588–594 (1994); Maecher et al., FASEB 11: 428–442 (1997). Sarcospan is tightly associated with the sarcoglycans to form a subcomplex of the DGC (Crosbie et al., J. Cell Biol. 145: 153–165 (1999). The function of the sarcoglycan-sarcospan complex is currently unknown. One hypothesis is that it stabilizes α-dystroglycan at the membrane. Another hypothesis is that the sarcoglycan-sarcospan complex may be important in the signaling functions of the DGC, a possibility which remains relatively unexplored.

Defects in components of the DGC have been implicated in muscle disorders manifested by muscle weakness and wasting. Currently, it is known that six forms of muscular dystrophies are caused by primary genetic defects within components of the DGC. These include Duchenne and Becker muscular dystrophies, the most prevalent forms of muscular dystrophies that are caused by mutations in the dystrophin gene and four forms of autosomal recessive limb-girdle muscular dystrophies (LGMD2-C, -D, -E and -F) caused by primary mutations in each of the four sarcoglycan genes (Straub and Campbell, Curr. Opin. Neurol. 10: 169–175 (1997). Additionally, mutations in the laminin-α2 chain cause a severe form of congenital muscular dystrophy. Recent data suggests that dystroglycan is important in basement membrane formation (Henry and Campbell, Cell 95: 859–870 (1998) and dystroglycan-null mice die at a very early embryonic stage (Williamson et al., Hum. Mol. Genet. 6: 831–841 (1997). It is likely that human-null mutations in the dystroglycans would also lead to an early embryonic lethality. In contrast, disruption of the α1-syntrophin gene in mice was not lethal, and also did not result in muscle degeneration (Kameya et al., J. Biol. Chem. 274: 2193–2200 (1999). However, neuronal nitric oxide synthase, which is usually localized at the sarcolemma through α1-syntrophin, was not found at the sarcolemma in these animals (Kameya et al., J. Biol. Chem. 274: 2193–2200 (1999).

To investigate the function of sarcospan, a sarcospan-deficient mouse was generated and characterized. The mouse generated was observed to exhibit an obese phenotype. Obesity in humans is a widespread and serious disorder, affecting a high percentage of the adult population in developed countries. Few persons suffering from this disorder are able to permanently achieve significant weight loss. This failure to treat obesity may be at least partially attributed to the complexity of the disease. An understanding of the genetic factors that underlie obesity may aid in treatment. Animal models are useful in developing this understanding. Current mouse models for obesity include obese (ob), agouti (wt), tubby (tub), fat and diabetes (db). These animal models are extremely useful for their ability to simplify the heritability of an otherwise very complex trait.

SUMMARY OF THE INVENTION

In one aspect, the present invention relates to a mouse, and cells derived therefrom, homozygous for a disrupted sarcospan gene, wherein the disruption in the gene is introduced into the mouse or an ancestor of the mouse at an embryonic stage, wherein the disruption prevents the synthesis of functional sarcospan in cells of the mouse. The mouse is characterized as weighing substantially more, and having substantially larger deposits of white adipose tissue, as compared to an otherwise genetically identical mouse lacking a disrupted sarcospan gene. In one embodiment, the introduced disruption comprises a deletion in a portion of the sarcospan gene. One such deletion is a region of about 7.6 kb, including 223 base pairs of intron 1, the entire exon 2, the entire intron 2, and 1800 base pairs of exon 3, and replacement of the deleted region with a PGK-neomycin resistance cassette as a marker for neomycin resistance. This deletion can be made by introducing into embryonic stem cells, a DNA construct comprising 2132 base pairs of intron 1 and 2220 base pairs of exon 3 of the sarcospan gene; and a neomycin resistance gene inserted between the portion of intron 1 and exon 3 of the sarcospan gene listed in a), the neomycin resistance gene being in the opposite transcriptional orientation as the sarcospan exons replaced; wherein the introduced construct lacks 223 base pairs of intron 1, the entire exon 2, the entire intron 2, and 1880 base pairs of exon 3, of the sarcospan gene.

In another aspect, the present invention relates to a method for diagnosing an individual with a clinical disorder associated with reduced expression of sarcospan. The method comprises providing a tissue biopsy sample from the individual and then quantitatively detecting sarcospan expression in cells of the sample. Sarcospan expression is also quantitatively detected in a comparable control sample obtained from a control individual known to exhibit normal expression of sarcospan, by otherwise identical means. The amount of sarcospan expression detected in the sample is compared to the amount of sarcospan expression detected in the control sample, with a substantially lesser amount of sarcospan expression in the former by comparison being indicative of the clinical disorder in the individual. The tissue biopsy is obtained from either skeletal muscle, cardiac muscle, brown adipose tissue, white adipose tissue, smooth muscle, vascular smooth muscle. In one embodiment, detection of sarcospan expression is accomplished by immunoassay for the sarcospan protein. In another embodiment, detection of sarcospan expression is accomplished by detection of the sarcospan mRNA, preferably by RNA blot analysis or reverse transcriptase polymerase chain reaction.

In another aspect, the present invention relates to a method for diagnosing an individual with a clinical disorder associated with a mutation in the sarcospan gene. The method comprises isolating nucleic acids encoding the sarcospan gene, or a portion thereof, from the individual and then analyzing the nucleic acids by means to identify a mutation predicted to alter sarcospan expression or function in comparison to wild-type, with identification of the mutation being indicative of the presence of the clinical disorder in the individual. In one embodiment, the means to identify a sarcospan mutation is PCR amplification of one or more regions of the sarcospan gene followed by analysis of the size of the amplified product or sequencing of the amplified product.

In another aspect, the present invention relates to a therapeutic method for treating an individual diagnosed with a clinical disorder associated with a mutation in the sarcospan gene. The method comprises providing an expression vector containing a nucleic acid encoding the wild-type form of the sarcospan protein; and introducing the expression vector into cells of the individual under conditions appropriate for expression of the wild-type form of the sarcospan protein. Suitable cells for introduction of the expression vector are white adipose cells, brown adipose cells, and skeletal muscle cells. In a preferred embodiment, the expression vector used is an adenovirus vector or an adeno-associated virus vector.

Another aspect of the present invention relates to a method for identifying therapeutic agents for the treatment of an individual diagnosed with a clinical disorder associated with a sarcospan mutation. The method comprises providing a mouse homozygous for a disrupted sarcospan gene, administering a candidate therapeutic agent to the mouse, and assaying for therapeutic effects on the mouse resulting from administration of the candidate therapeutic agent. Methods for identifying an agent which reduces weight gain in an individual are also proposed. In addition, a method for identifying the presence of a specific double polymorphism in exon 3 of the human sarcospan gene is also presented.

DETAILED DESCRIPTION OF THE INVENTION

Figure 1:
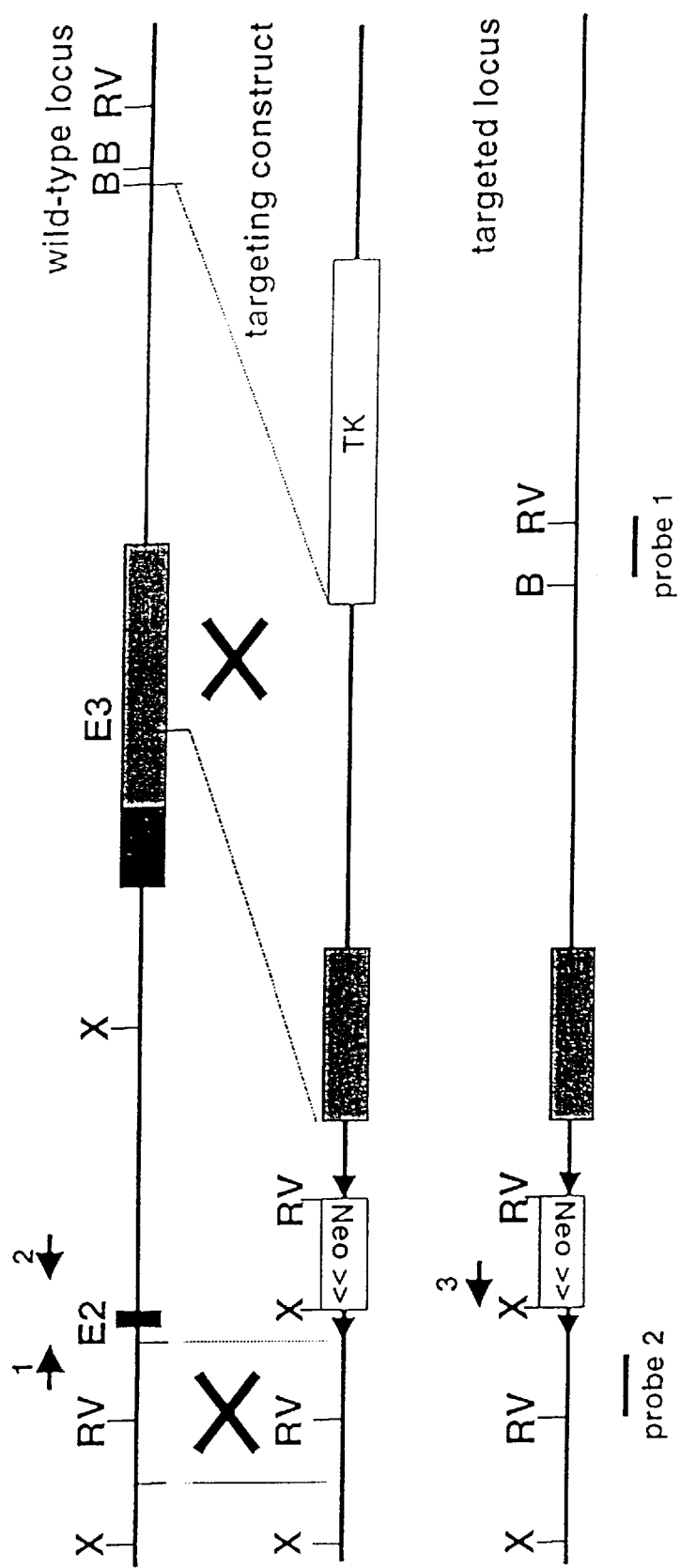
FIG. 1 is a schematic representation of the generation of sarcospan-deficient mice by homologous recombination in embryonic stem cells. Shown are restriction maps of the wild-type sarcospan locus, the targeting construct and the targeted locus. A 7.6 Kb region including exons 2 and the coding region of exon 3 (in black) was deleted and replaced by a phosphoglycerate kinase-neomycin cassette (Neo). Also shown are probes 1 and 2 below, positioned at their regions of homology to the targets. Primer binding sites for primers 1 (SPNi1FA), 2 (SPNi2RA), and 3 (NEOspnKO) are denoted by arrowheads. RV indicates the location of EcoRV restriction endonuclease sites. B indicates the location of BamHI sites, X indicates the location of XbaI sites.

The present invention is based on the generation and characterization of a mouse which does not express the sarcospan gene. The mouse is homozygous for a disrupted sarcospan gene, wherein the disruption prevents the synthesis of functional sarcospan in all cells of the mouse. Such a mouse is referred to herein as sarcospan-deficient, or alternatively as sarcospan-(Sspn-) null.

The present invention relates, in one aspect, to a sarcospan-deficient mouse. The sarcospan-deficient mouse characterized in the Exemplification section below was generated by introducing a disruption into a single copy of the sarcospan gene of an ancestor of the mouse at an embryonic stage, to produce a heterozygous genomic mutation. Resulting heterozygotes of the opposite sex were then bred to produce homozygotes in a Mendelian ratio of inheritance.

The specific disruption introduced into the sarcospan gene was a deletion. Those of skill in the art will recognize that a sarcospan-deficient mouse can be produced by introduction of a variety of disruptions into the mouse genome. To produce a sarcospan deficient mouse of the present invention, an introduced disruption should prevent synthesis of functional sarcospan in all cells of the mouse, when present in a homozygous state or in concert with another non-functional sarcospan allele. Preferably the disruption is introduced directly into the sarcospan gene. Possible disruptions include, without limitation, insertions of nucleic acid sequences into the sarcospan gene and deletion of nucleic acid sequences of the sarcospan gene. An insertion should include nucleic acid sequences predicted to disrupt expression of wild-type sarcospan (e.g., a stop codon, a missense mutation, a frame shift mutation, etc.). Similarly, a portion deleted from the gene should include sequences predicted to significantly affect expression or function of the sarcospan gene product (e.g., coding region, splicing signal, regulatory sequences, etc.). Preferably, the disruption results in the complete loss of expression of sarcospan, but may alternatively result in the production of a non-functional product (e.g., a truncated product, or a fusion protein). Alternatively, inhibition of sarcospan gene expression may be accomplished by disruption of regulatory sequences, such as promoter and enhancer elements. The end product sarcospan-deficient mouse may have two copies of an identically disrupted sarcospan allele, or alternatively, each copy may contain a distinct disruption.

The skilled artisan will be aware of numerous other methods for generating a sarcospan-deficient mouse. The skilled artisan will also realize that a sarcospan deficiency can also be produced in other animal species to generate other sarcospan-deficient animals. It is the intent of the present invention to encompass all such equivalents. The present invention also encompasses all cells, tissues, organs, and progeny derived from the sarcospan-deficient animal described herein.

The sarcospan-deficient mouse of the present invention exhibits phenotypic differences when compared to an otherwise genetically identical mouse lacking a disrupted sarcospan gene. (Comparison of the sarcospan-deficient mouse to the control mouse was made under conditions wherein all mice were raised and maintained in the same environment under the same conditions). One such difference in phenotype relates to body weight. The sarcospan-deficient mouse of the present invention weighs substantially more and has substantially larger deposits of white adipose tissue as compared to the control mouse, when fed identical food and allowed to eat and drink at will. The Exemplification section below details experiments which characterize the sarcospan-deficient mouse as weighing 15% to 20% more on average than the wild-type mouse maintained under the specified conditions. There is a certain amount of heterogeneity in the obesity phenotype in that some of the mice weigh as much as 50% more than the average wild-type mouse. At least a portion of this increase in weight results from the accumulation of larger deposits of white adipose tissue. Without wishing to be bound by theory, the increased weight gain and fat deposits are thought to reflect a disruption in metabolic signalling events.

The phenotype of the sarcospan-deficient mouse of the present invention indicates that the sarcospan molecule plays a significant role in either direct or indirect regulation of an animal's body weight. Without wishing to be bound by theory, sarcospan is thought involved in regulation of metabolism. Importantly, results presented in the Exemplification section below indicate that the absence of functional sarcospan in an individual, such as a human, contributes to one or more clinical disorders. A clinical disorder that is associated with or directly caused by a reduction or absence of wild-type sarcospan in the diagnosed patient is referred to herein as a sarcospan disorder. A sarcospan disorder may result from aberrant expression of a sarcospan gene or aberrant function of an expressed sarcospan protein. Symptoms or manifestations of a sarcospan disorder may include, without limitation metabolic abnormalities such as weight gain or obesity, increased percent body fat, and increased appetite, as compared to an individual known not to have a sarcospan disorder. One of skill in the art would predict from the phenotype of the sarcospan-deficient mouse that an individual with reduced or absent wild-type sarcospan is at risk for development of a number of other clinical disorders and complications known to arise from metabolic abnormalities. Causes of a sarcospan disorder are not limited to loss or decrease in function of wild-type sarcospan, in that overproduction or overactivity of sarcospan in an individual is also expected to produce a clinical disorder which manifests as abnormal weight or metabolism.

A sarcospan disorder may arise from a number of potential genetic defects. Aberrant (reduced or increased) expression of wild-type sarcospan, possibly resulting from a mutation in sarcospan gene regulatory sequences, or a mutation in a regulatory protein of sarcospan gene expression or protein function is expected to lead to a sarcospan disorder. Alternatively, expression of a mutant sarcospan protein having impaired function would lead to a sarcospan disorder. All animals known to express sarcospan (e.g., rodents, canines, felines, equines, and primates, especially humans) may potentially have a sarcospan disorder, and can be diagnosed as such by the methods described below.

In another aspect, the present invention relates to a method for diagnosing an individual with a clinical disorder associated with reduced expression of sarcospan. Such reduced expression may arise from reduction in gene expression, reduction in protein stability (e.g., resulting from a mutation), improper post-translational processing, or improper subcellular protein delivery. Such a diagnosis is made by detecting a reduced amount of sarcospan expression in the individual as compared to the amount of sarcospan expression in control individual known not to have a sarcospan disorder. For instance, a tissue biopsy sample is obtained from the individual and cells of the sample are processed for quantitative detection of sarcospan expression. The quantity of detected sarcospan expression is compared to that of a comparable sample obtained from the control individual, preferably by identical means of detection. The two determined amounts are compared and a substantially lesser amount of sarcospan expression as compared to the control is indicative of the clinical disorder in the individual. A control sample is generally obtained from the control patient by the same means as the initial sample was obtained to produce a comparable sample. Determination of what constitutes a comparable sample is within the ability of the skilled practitioner. A substantial decrease in sarcospan expression is defined as a reproducibly detected decrease in sarcospan expression in the individual as compared to a comparable control individual known not to have a sarcospan disorder. A complete lack of detection of sarcospan is regarded as a substantial decrease. At least a 10-fold difference in expression as compared to a control individual would be regarded as a substantial decrease. It is also likely that smaller differences in sarcospan expression (e.g., between 2-fold and 10-fold difference in expression levels) also correlates with a clinically detectable sarcospan disorder, potentially with milder associated symptoms.

The diagnosed individual may be exhibiting symptoms of obesity or other such symptoms of abnormal metabolic regulation, or alternatively be at risk for the development of such symptoms, as possibly determined by family history.

Tissues suitable for biopsy in the above-described method are tissues in which sarcospan is normally expressed. Such tissues include, without limitation, thymus, prostate, testis, ovary, small intestine, colon, spleen, heart and brain (Crosbie et al., *J. Biol. Chem.* 272: 31221–31224 (1997). Preferably, the biopsy is obtained from skeletal muscle, cardiac muscle, brown adipose tissue, white adipose tissue, smooth muscle, or vascular smooth muscle.

Sarcospan expression in the biopsied tissue cells can be quantitatively detected by a number of techniques known in the art. Techniques which quantitatively detect the protein product are useful in this respect, and are generally performed by immunoassay (e.g., ELISA, protein or Western blot analysis, and immunofluorescence). Antibodies which specifically recognize the sarcospan protein are known in the art and available to or easily generated by the skilled practitioner. Certain immunoassay-based techniques also provide information regarding the protein product, (e.g., size and subcellular localization) which may also serve as an indicator of aberrant sarcospan expression or function.

Techniques which quantitatively detect the amount of sarcospan MRNA are also useful for diagnosis. Such techniques are generally performed using a hybridization-based assay (e.g., RNA or Northern blot analysis, reverse transcriptase polymerase chain reaction (RT-PCR). Probes appropriate for detection of sarcospan mRNA in Northern blot analysis are a sarcospan cDNA or a portion thereof which specifically hybridizes to sarcospan mRNA under stringent conditions. Primers for RT-PCR analysis of sarcospan expression can be determined by one of skill in the art. Such assays are utilized to determine RNA size and sequence, which may also serve as an indicator of aberrant expression or protein function. These assays can also potentially cross react with a mutant sarcospan allele which is expressed at normal levels but is impaired in function. Therefore a negative result does not necessarily rule out the presence of a sarcospan disorder.

In another aspect, the present invention relates to a method for diagnosing an individual with a clinical disorder associated with a mutation in the sarcospan gene. Several of the techniques described above are useful in identifying mutations in the sarcospan gene coding region. Alternatively, the individual's sarcospan gene may be directly analyzed by isolating nucleic acids encoding the sarcospan gene, or a portion thereof, from the individual. Useful portions of the gene for analysis include any length of sequence suitable for analysis by the chosen assay, the sequence being considered susceptible to a mutation which affects sarcospan expression or function (e.g., exon, intron, upstream coding region, coding sequences, etc.). Isolated nucleic acids are then analyzed by means to identify a mutation in the sequence known or predicted to alter sarcospan expression or function. A mutation in the sequences is detected by analyzing the sequence, either by direct sequencing, or by indirect assay (e.g., hybridization or other characteristic physical properties of the sequence). In addition, analysis of the size of the sarcospan gene, or specific portions thereof (e.g., an intron, an exon, or a restriction fragment), may also indicate a mutation. Identification of such a mutation is indicative of the presence of the clinical disorder. Examples of such a mutation are a nonsense mutation, a non-conservative missense mutation, an insertion or deletion which changes the reading frame, a mutation which alters a splice junction, a mutation which alters regulation of transcription, a gross rearrangement or translocation of the gene. Function of a mutant sarcospan protein is determined altered by comparison to the function/activity of wild-type.

Analysis should be performed on both copies of the sarcospan gene in the individual. An individual who is diagnosed as having a mutation in both copies which affects sarcospan expression or function is considered to have a sarcospan disorder. Data presented in the Exemplification section below indicates that an individual who is heterozygous for such a sarcospan mutation may be asymptomatic. However, gain of function and dominant negative mutations of proteins are known to occur, and such a mutation would be predicted to affect a homozygous individual.

One technique for analysis of the sarcospan gene is PCR amplification of one or more regions of the sarcospan gene, followed by size analysis of the amplified product. A detectable difference in size of the amplified product, as compared to that from identically amplified wild-type gene, is an indication of the presence of a mutation. A mutation which alters the size of the amplified product is likely to alter sarcospan expression or function, and should be further analyzed (e.g., by sequencing the amplified region). Some mutations which affect gene expression or protein function may not alter the size of the amplified region, and must be identified by other techniques, such as direct sequencing. Regions preferred for amplification include coding regions of the sarcospan gene (e.g., exon 1, exon 2, and exon 3). As mutations which affect expression and function have also been known to occur in non-coding regions, examination of non-coding regions (e.g., intron 1 and intron 2) is also preferred.

The function of an identified mutant protein can be analyzed by introducing or expressing the protein in an in vitro system and comparing the properties of the mutant to those of wild-type. For instance, the Chinese hamster ovary (CHO) cell swelling assay described in the Exemplification section below may be utilized to determine if a mutant sarcospan protein exhibits the same properties in this assay as wild-type. A detectable difference in the properties (e.g., reduced or increased swelling of the CHO cells in hypoosmotic conditions) indicates altered protein function.

Studies of sarcospan expression and function in a population of animals which exhibit a range of metabolic regulation phenotypes will provide useful clinical information. Such data can be used to correlate specific sarcospan mutations with clinical disorders occurring in the population. Preferably, the surveyed population is human, although surveying an animal model population, such as mouse or rabbit, may also be of benefit. The different alleles of the sarcospan gene present in individuals of the population are analyzed by the methods described above, and specific polymorphisms identified in the population are correlated with clinical disorders of the individuals in which they are identified. Statistically significant correlations that are identified will indicate clinical disorders commonly associated with a sarcospan mutation.

Another aspect of the present invention is a method for treating an individual diagnosed with a sarcospan disorder. Restoration of a functional sarcospan gene in such an individual is expected to have a therapeutic effect. Such restoration is achieved by introducing an expression vector containing a nucleic acid encoding the wild-type form of the sarcospan protein into cells of the individual under conditions appropriate for expression.

Cells of the individual appropriate for targeted introduction of the expression vector are cells known to naturally express the wild-type sarcospan gene, discussed above. In the absence of restoring wild-type sarcospan expression to all such cells in the individual, restoration of wild-type sarcospan expression in a subset of these cells is expected to provide significant therapeutic benefit. Preferably, targeted cells include, without limitation, white adipose cells, brown adipose cells, and skeletal muscle, as the experiments presented herein indicate that sarcospan expression in these cells is of particular functional significance.

Expression vectors currently known in the art and suitable for use in the above described method include, without limitation, adenovirus-based expression vectors, described by Gregory et al., (1997) U.S. Pat. No. 5,670,488; McClelland et al., (1998) U.S. Pat. No. 5,756,086; Armentano et al., (1998) U.S. Pat. No. 5,707,618; Saito et al., (1998) U.S. Pat. No. 5,731,172, the contents of each are incorporated herein by reference. Also included are gutted adenovirus delivery systems (Clemens et al., *Gene Therapy* 3: 965–972 (1996), and adeno-associated virus (AAV) based vectors, some examples of which are described by Podsakof et al., (1999) U.S. Pat. No. 5,858,351; Carter et al., (1989) U.S. Pat. No. 4,797,368; Lebkowski et al., (1992) U.S. Pat. No. 5,153,414; Srivastava et al., (1993) U.S. Pat. No. 5,252,479; Lebkowski et al., (1994) U.S. Pat. No. 5,354,678; Wilson et al., (1998) U.S. Pat. No. 5,756,283, the contents of each being incorporated herein by reference. In a preferred embodiment, the expression vector is an adenovirus vector or an adeno-associated virus vector. The production of an adenovirus expression vector that encodes sarcospan is described in the Exemplification section below.

The nucleic acid that encodes the sarcospan protein is a sarcospan cDNA, genomic DNA, or any combination of DNA sequences from which translation will produce wild-type sarcospan protein. Preferably, the nucleic acids have a sequence derived from, or which encode a sarcospan protein of the species in which it is to be introduced. Significant benefit may result from the inclusion of gene regulatory elements (e.g., promoter elements) that are specific for the sarcospan gene.

The sarcospan-deficient animal of the present invention is useful as an animal model system for diseases and conditions associated with sarcospan deficiency or reduction in sarcospan function. Such a model system is also used for identifying therapeutic agents and/or treatments of the disease. A number of disorders or complications may arise from improper regulation of metabolism (e.g., unusual weight gain, appetite abnormalities, increased percent body fat, abnormal glucose levels). The manifestation of such disorders is often influenced by the environment (e.g., diet, exercise) and overall health of the individual. The sarcospan deficient animal of the present invention can be used to study the effects of such influences on the disease state.

The present invention relates, in another aspect, to a method for identifying therapeutic agents for treatment of an individual diagnosed with a clinical disorder associated with a sarcospan mutation. Generally, an animal exhibiting symptoms of a specific clinical disorder is used. The sarcospan-deficient animal is administered a candidate therapeutic agent. The mouse is then assayed for therapeutic effects resulting from the administration of the candidate therapeutic agent, as determined from the use of appropriate experimental controls. Therapeutic effects are indicated by a reduction or reversal of symptoms or amelioration of the general condition of the mouse. This method is useful for identifying therapeutic agents for treatment of any of the sarcospan disorders described above. Screening of candidate therapeutic agents such as small molecules from molecular libraries, presently known drugs, and molecules for use in gene therapy, will identify therapeutic agents for treatment of a human patient diagnosed with a sarcospan disorder similar to that of the animal model used. The route of administration (e.g., oral, intravenous, intramuscular, intraperitoneal, etc.) of the candidate therapeutic agent will depend upon the agent itself, and can be determined by one of average skill in the art. This model system can also be used for the identification of optimal methods of delivery and vectors for use in the gene therapy methods described above. This method can also be adapted to identify agents which prevent the development of a clinical disorder in an individual with a sarcospan deficiency, for instance by administering the candidate agent to an asymptomatic sarcospan-deficient animal, and then subjecting the animal to conditions expected to bring on the disorder.

The sarcospan-deficient animal of the present invention is also useful for identifying agents which reduce weight gain in an individual. The obese phenotype of the sarcospan-deficient mouse can be used to screen agents for properties which reduce or inhibit weight gain or which promote weight loss in an individual with a genetic tendency to accumulate above average fat deposits. The sarcospan-deficient animal (e.g., a mouse) is administered a candidate agent and then monitored for effects of the agent on the weight of the mouse. A reduction in weight gain, in overall weight, or in the fat deposits of the mouse, as compared to the appropriate controls, serves as an indication that the administered agent can be used for similar weight control of an individual such as a human. Agents identified for use can be applied to human patients suffering from metabolic regulatory disorders such as obesity, including, but not limited to, sarcospan disorders.

One of skill in the art will recognize that the conditions in which the sarcospan-deficient mouse is maintained is expected to affect the above screens for therapeutic and weight loss promoting agents. It is within the ability of the skilled practitioner to determine and apply the necessary conditions for each specific screening process undertaken.

In another aspect, of the present invention relates to a method for identifying the presence of a double polymorphism in an individual. The double polymorphism occurs in exon 3 of the human sarcospan gene. The first polymorphism occurs at nucleotide 556 and the second polymorphism occurs at nucleotide 681 of the sarcospan gene. Because the polymorphisms always occur together, identification of the presence of one, indicates the presence of the other. This is achieved by obtaining or generating a double stranded nucleic acid which corresponds to exon 3 of the individual's sarcospan gene. That nucleic acid is then assayed for i) the absence of an HgaI site at the nucleotide corresponding to nt 556 of the sarcospan gene, and ii) the presence of an MaeII restriction site at the same position. Detection of an absence of the HgaI site in combination with detection of the MaeII site is an indication of the presence of the double polymorphism. The identified double polymorphism is useful for performing genetic linkage studies.

EXEMPLIFICATION

Generation of sarcospan-deficient mice

To generate sarcospan-deficient (Sspn-null) mice, genomic DNA clones from a 129/SVJ genomic library were isolated by hybridization screening with a mouse EST corresponding to a portion of the 3' UTR of mouse sarcospan. Isolated clones were analyzed by restriction enzyme digestion and DNA sequencing. From these genomic clones, a targeting vector was designed to replace exon 2 and the coding sequence of exon 3 of sarcospan, which encodes for three of the four transmembrane domains, the extracellular loop, and the C-terminal intracellular domain of sarcospan. Southern blot analysis of 236 neomycin-resistant embryonic stem (ES) cells demonstrated homologous recombination in nine independent clones.

Southern blot analysis using probe 1 identified a 16.2 Kb EcoRV fragment in the wild-type locus, and a 7.5 Kb fragment in the targeted allele locus. Only the 16.2 Kb fragment was identified in ES +/+ cells, while both bands were identified in the ES +/- cells, indicating the presence of one wild-type locus and one targeted locus.

Two of the ES +/- clones produced were used to generate chimeric founder mice. Heterozygous mice from the F1 generation were identified by genotype analysis via PCR. Primers 1 (SPNi1FA) and 2 (SPNi2RA) amplified a 840 bp PCR product from the wild-type allele (+/+); primers 1 (SPNi1FA) and 3 (NEOspnKO) amplified a 425 bp product from the null allele (-/-). Heterozygotes were crossed to obtain Sspn-null mice. Sspn-null mice were born from heterozygous matings in a predicted Mendelian inheritance frequency and the homozygous null mice were indistinguishable from their wild-type or heterozygous littermates upon gross examination. Northern blot analysis of skeletal muscle from wild-type, heterozygous, and homozygous Sspn-null mice revealed a 4.5 Kb sarcospan-specific band present in samples from the wild-type and heterozygous mice, but not in skeletal muscle of the Sspn-null mice.

The presence of two copies of the Sspn-null allele in the Sspn-null mice was further verified by protein analysis. No sarcospan protein could be detected by immunofluorescence analysis of skeletal, cardiac or smooth muscle from the Sspn-null animals using two separate antibodies generated against either the N-terminal, or C-terminal domains of the protein. Transverse cryosections (7 µM) of quadriceps muscles from control or Sspn-null animals were stained with the anti-sarcospan specific antibodies. In the control muscle, sarcospan was present at the sarcolemma and within neuromuscular junctions of the skeletal muscle. In the Sspn-null muscle, the antibodies failed to detect sarcospan protein. Similarly, immunoblot analysis of total homogenates or KCl-washed microsomes (membrane enriched) from the Sspn-null animals, failed to detect the sarcospan protein, but detected a strong band which migrated at 20 KDa, in identical samples obtained from wild-type and heterozygote mice. The failure to detect the N-terminal cytoplasmic domain of mouse sarcospan, encoded by Exon 1 which was not deleted in the null-mice, further demonstrated that a true null allele was generated.

Sarcospan-deficient animals do not develop an early-onset muscular dystrophy phenotype To examine the effect of the loss of sarcospan on skeletal muscle morphology, transverse cryosections (10 µM) of quadriceps, biceps, diaphragm, and neck muscles were stained with hematoxylin and eosin (H & E)[?]. The skeletal muscle morphology of the Sspn-null muscles were similar to that of the wild-type control and heterozygous animals and failed to exhibit any hallmarks of a progressive muscular dystrophy. To analyze the integrity of the sarcolemma in Sspn-null animals, Evans blue dye was injected through the retro-orbital sinus and the animals were sacrificed 3 hr after injection by cervical dislocation. Cryosections of skeletal muscle were analyzed microscopically for evidence of Evans Blue uptake in the muscle fibers. There was no evidence of Evans Blue uptake in either the wild-type control, or Sspn-null muscles. To further demonstrate sarcolemmal integrity of the Sspn-null muscles, quantitative serum creatine kinase assays were performed on age and sex-matched control, heterozygous, and Sspn-null mice. Wild-type control, heterozygous and Sspn-null animals all exhibited similar, low levels of serum creatine kinase levels.
Other components of the dystrophin glycoprotein complex are maintained at the sarcolemma in Sspn-null animals To evaluate the consequences of the loss of sarcospan on the expression of the other components of the dystrophin glycoprotein complex (DGC), immunofluorescence analysis was carried out on cryosections of skeletal, cardiac, and smooth muscle from control and Sspn-null mice. The sarcoglycans (α, β, γ, δ, and ε), α- and β-dystroglycan, and dystrophin were all maintained at the sarcolemma in the Sspn-null mice. To verify that the proteins were maintained at the sarcolemma, immunoblot analysis was performed on KCl-washed microsomes obtained from wild-type, heterozygous, or Sspn-null skeletal muscle. The respective samples were probed with antibodies specific for either α-, β-, γ-, δ-, and ε- sarcoglycan, α- and β-dystroglycan, and dystrophin. Each of these components were detected at similar levels in the respective samples. This analysis further confirmed that the loss of sarcospan did not affect the expression of the other components of the dystrophin-glycoprotein complex in skeletal muscle.

Sarcospan-deficient animals are obese

Figure 2:
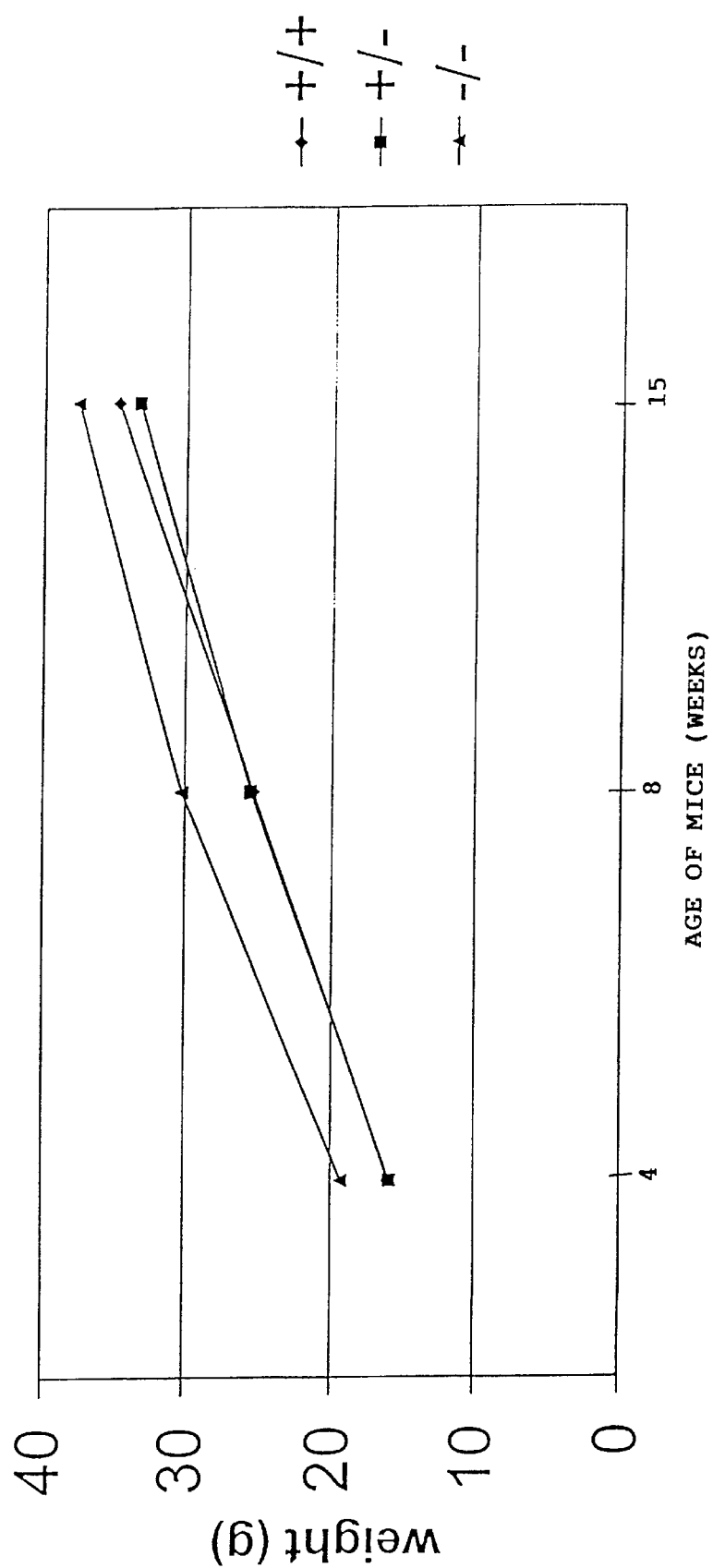
FIG. 2 is a graphic representation of the elevated weight of Sspn-null (−/−) male mice compared to male wild-type (+/+), and heterozygous (+/−) mice at ages 4, 8, and 15 weeks.
Figure 3:
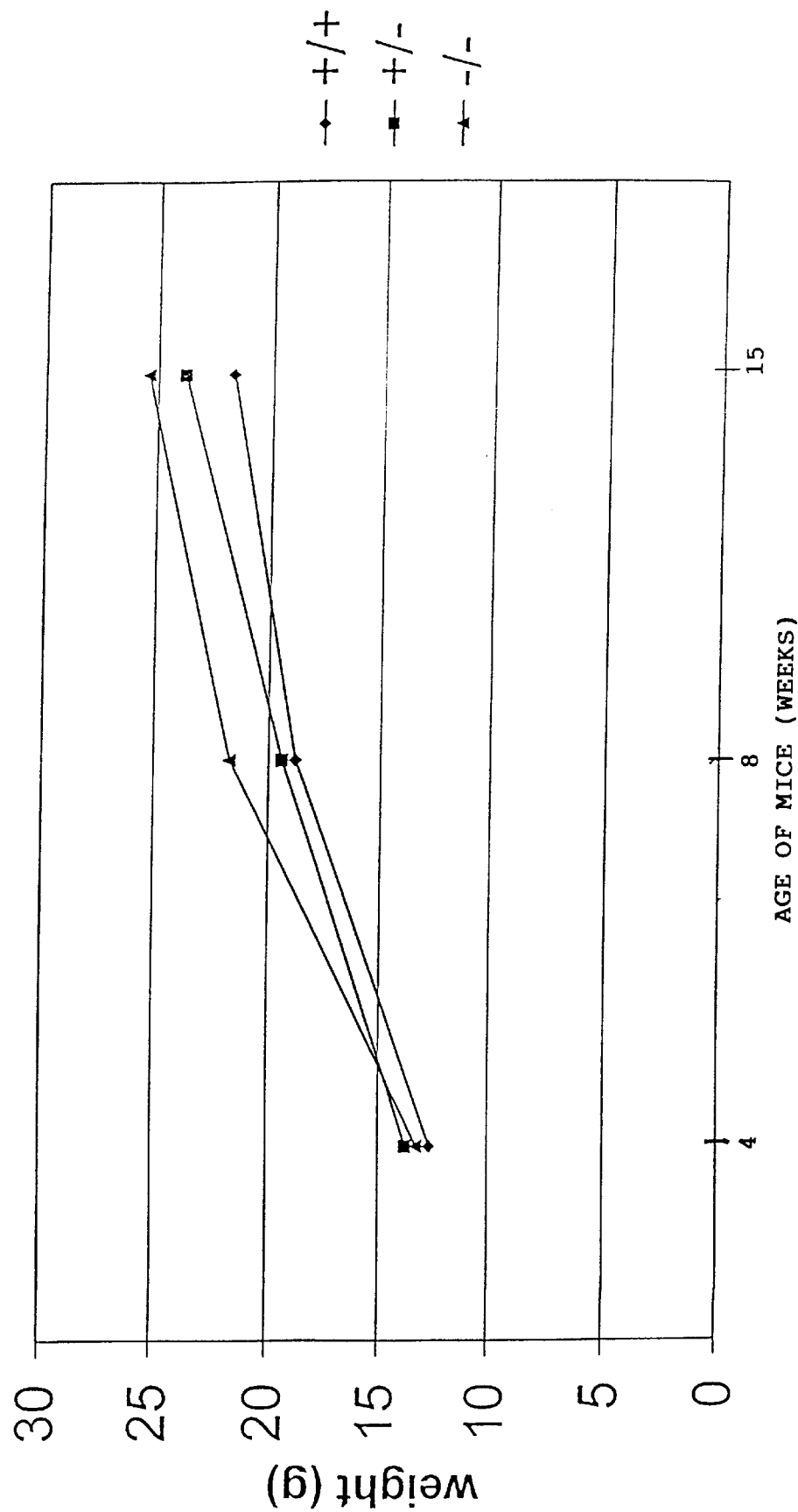
FIG. 3 is a graphic representation of the elevated weight of Sspn-null (−/−) female mice compared to female wild-type (+/+), and heterozygous (+/−) mice at ages 4, 8, and 15 weeks.

Visual inspection of the sarcospan-deficient mice indicated that they seemed larger than their control littermates. To address this observation, the weights of the Sspn-null mice were compared to that of age and sex match controls. On average, male Sspn-null animals weigh 20% more than their age- and sex-matched wild-type or heterozygous counterparts (FIG. 2) when maintained under conditions where they were allowed to eat at will. Female Sspn-null animals weighed 15% more than their age- and sex-matched wild-type or heterozygous counterparts (FIG. 3). Gross observation upon dissection of the animals indicated that the Sspn-null animals had much larger deposits of white adipose tissue. Of particular note was the subcutaneous fat pad of the hind limbs, the epididymal fat pad (males) or the omental fat pad (females) and the retroperitoneal fat pad. Additionally, the Sspn-null animals had a greater amount of fat surrounding their organs.

Figure 4:
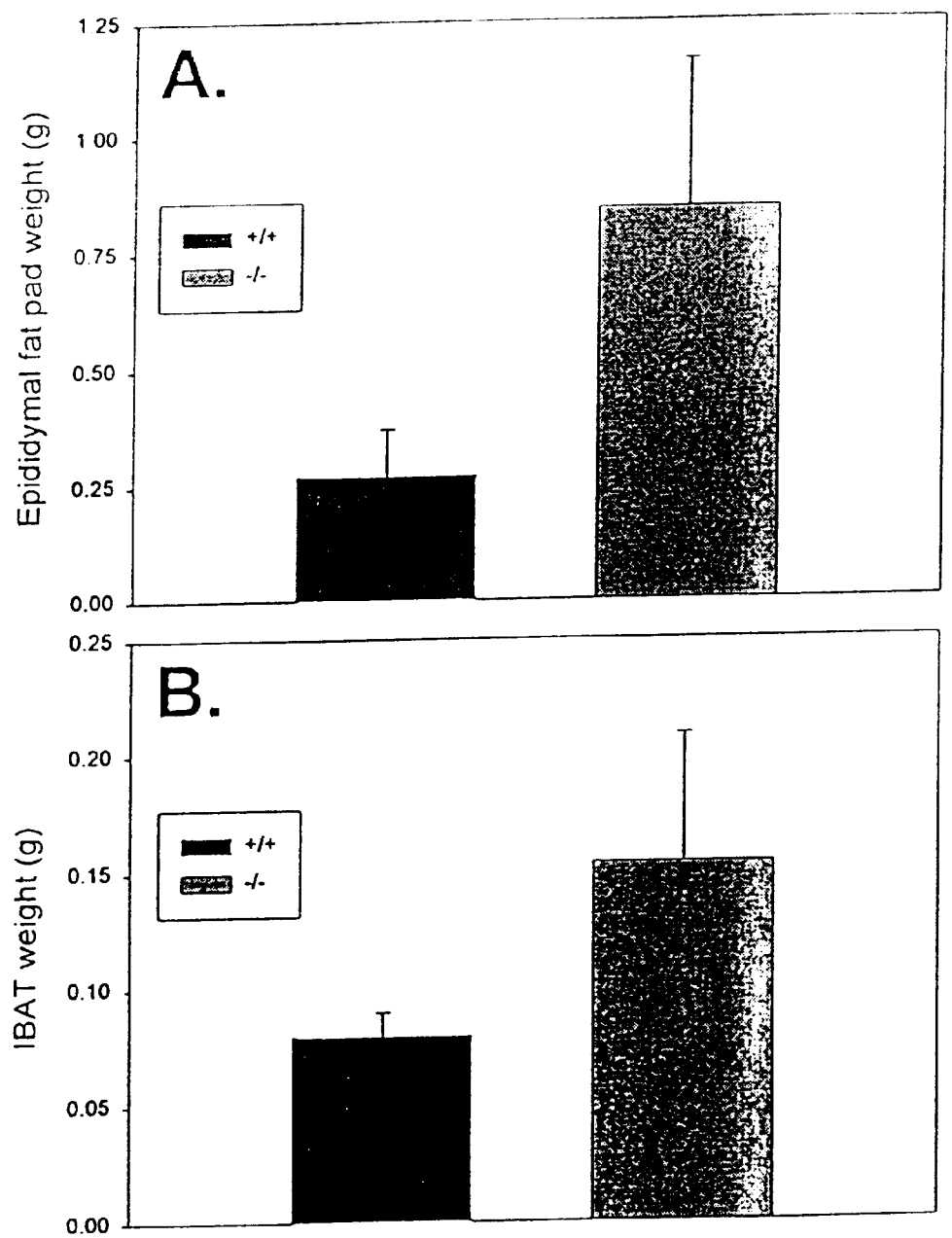
FIG. 4 consists of bar graphs which quantitatively compare the fat deposits of Sarcospan-deficient mice versus wild-type mice. Panel (A) quantitates epididymal fat pad weights (g) of wild-type (dark bar)(n=5) and Sspn-null male (light bar) (n=6) 10-week old mice. Panel (B) quantitates intrascapular brown adipose tissue weight of wild-type (dark bar) (n=5) and Sspn-null male (light bar)(n=6) 10-week old mice. Error bars indicate one standard deviation from the mean.

To quantify this increase in fat deposits, the intrascapular brown adipose tissue and the epididymal white adipose tissue were carefully removed from 10 week old male mice and their weights compared to that of identically obtained tissues from the wild-type animals (FIG. 4). The mean weight of the epididymal fat pad in the control mouse was 0.272 g (+/−0.1 g) while the mean weight of the epididymal fat pad in the sarcospan-deficient animals was 0.845 g (+/−0.32 g) (FIG. 4A). The intrascapular brown adipose tissue of the sarcospan-deficient animals was also much larger than the wild-type animals (0.154 g, +/−0.05 g vs. 0.08 g +/ −0.01 g, FIG. 4B).

Sarcospan is expressed in brown adipose tissue

To begin to address the mechanism behind the observed obesity, total RNA was isolated from brown adipose tissue obtained from control mice, and reverse transcriptase PCR was performed to analyze whether the sarcospan transcript was present in these tissues. Sarcospan-specific products were amplified as expected from control skeletal muscle RNA. In addition, sarcospan-specific products were also amplified from the brown adipose tissue, indicating that the sarcospan gene is expressed in these tissues. To confirm these results, immunofluorescence analysis was performed on brown adipose tissue from control and Sspn-null mice. Specific staining was observed in the brown adipose tissue from the control mice, but not in the Sspn-null tissue, using a sarcospan specific antibody probe.

To further investigate the tissue distribution of sarcospan expression, and the relationship of sarcospan expression to the expression of other members of the dystroglycan complex, immunoblot analysis was performed on total membranes isolated from brown and white adipose tissue, obtained from control and sarcospan-deficient mice. As expected, a sarcospan specific probe identified a 20 KDa sarcospan-specific band, representing sarcospan, in KCl-washed microsomes from skeletal muscle isolated from wild-type and heterozygous animals, but did not detect this band in the microsome preparation from sarcospan-deficient skeletal muscle. The same analysis also detected sarcospan in total membranes isolated from white and brown adipose tissue from the wild-type mice. Sarcospan was not, however, detected in the white or brown adipose tissue from the sarcospan-deficient mice. The tissue samples were concurrently analyzed for expression of proteins known to interact with sarcospan at the plasma membrane, including dystroglycan and α-, γ-, and ε-sarcoglycan. Western blot analysis detected dystroglycan and ε-sarcoglycan in the white and brown adipose tissue of wild-type mice. However, neither α- nor γ-sarcoglycan were detected in these tissues. Interestingly, dystroglycan and ε-sarcoglycan were detected in the sarcospan-deficient adipose tissue at levels similar to wild-type adipose tissue, suggesting that, as in skeletal muscle, expression and maintenance of these proteins at the plasma membrane is not dependent on sarcospan expression.

Sarcospan is expressed in differentiated 3T3 L1 adipocytes

To confirm that the sarcospan observed in the brown and white adipose tissue is derived from adipocytes and not from other cell types in the tissue, sarcospan expression in 3T3 L1 adipocytes was analyzed. Sarcospan was not detected in the undifferentiated 3T3 L1 fibroblasts by immunofluorescence analysis, but was detected by the same method at the plasma membrane of 3T3 L1 adipocytes which had been differentiated into adipocytes. Dystroglycan was detected at very low levels in the undifferentiated fibroblasts but levels were dramatically increased in the differentiated adipocytes. These data indicate that sarcospan and dystroglycan have roles in the normal physiology of adipocytes, and that these roles are perturbed in the absence of sarcospan, resulting in the observed obesity of the sarcospan-deficient mice.

Expression of sarcospan promotes cell swelling in hypoosmtic environment

A human sarcospan cDNA inserted into a pcDNA3 expression construct was found abundantly expressed in a Chinese hamster ovary (CHO) cell transfection system. In addition, sarcospan was also observed to be located at the CHO cell plasma membrane, as determined by surface biotinylation, as described in Crosbie et al. (*J. Cell Biol.* 145: 153–165 (1999). The sarcospan expressing cells were observed to be 2–3 times larger in surface area than their mock-transfected controls when in a hypoosmotic solution.

Identification of a polymorphism in exon 3 of the sarcospan gene

Two polymorphisms have been identified that occur within exon 3 of the human sarcospan gene. These polymorphisms were identified by sequence analysis of individuals within the normal population. The first polymorphism occurs at nt556 and results in an amino acid change, Ser 186Asn. The second polymorphism, which always co-migrates with the first polymorphism, occurs at nt681 and results in a Val227Ile change. The presence of these polymorphisms within the sarcospan gene can be rapidly identified by restriction digest. The normal sarcospan sequence contains an Hga I site at nt 556, which is not present with the polymorphic nucleotide substitution. Also, the presence of the polymorphism at nt 556 introduces a Mae II restriction site at that position. Exon 3 amplified from human genomic DNA served as suitable substrate for the restriction digest. Cleavage of the normal and polymorphic exon 3 PCR products with Hga I resulted in PCR products of 250 bp and 450 bp, respectively. Mae II did not digest the normal exon 3 PCR product (500 bp), but did cleave the polymorphic product into two fragments of 260 and 240 bp.

METHODS OF THE INVENTION

Isolation of murine sarcospan genomic and CDNA clones.

The murine sarcospan genomic DNA sequence was obtained by screening a 129SV mouse genomic library (Lambda FIX II, Stratagene, La Jolla, Calif.) using a mouse sarcospan EST (IMAGE clone: 406138 obtained from Research Genetics, Inc., Huntsville, Ala.) containing a portion of the sarcospan 3' UTR. Clones containing the sarcospan insert were analyzed by restriction enzyme mapping and DNA sequencing using dye terminator cycling on a 373 Stretch Fluorescent Automated sequencer (Applied Biosystems). 24 Kb of the sarcospan genomic DNA sequence was analyzed containing exons 2 and 3 and flanking regions. Murine sarcospan cDNA was isolated by screening a mouse skeletal muscle library (a generous gift of Dr. Jeffrey Chamberlain, University of Mich.) with the same EST. Clones were analyzed by DNA sequencing as above.

Generation of the Sspn targeting plasmid.

The Sspn targeting plasmid was constructed using a modified version of the positive-negative selection vector pPNT (obtained from Dr. Richard Mulligan, Whitehead Institute, Cambridge, Mass.) (Tybulewicz et al., *Cell* 65(7): 1153–63 (1991). A neomycin cassette flanked by lox P sites replaced the neomycin cassette from the original PPNT vector. The short arm of homology in the targeting vector was a 2.1 Kb BsaH1 fragment containing a 3' portion of intron 1. This fragment was inserted into the modified pPNT vector-in the Cla1 cloning site upstream of the PGK-neomycin resistance cassette. Orientation of this fragment was confirmed by restriction enzyme digestion and sequencing. To generate the long arm region of homology, a 10 Kb Nhel/Notl fragment containing a portion of the 3' UTR located in exon 3 and downstream sequences was isolated from a genomic clone and subcloned into pBluescript KS (+) (pBS). From this, a 6.5 Kb BamHI fragment was subsequently isolated and inserted into the BamHI cloning site distal to the PGK-neomycin resistance cassette. Orientation of this fragment was also confirmed by restriction enzyme digestion and sequencing. The vector contained a thymidine kinase cassette distal to the long arm. The targeting construct, as shown in FIG. 1, contained, from 5' to 3', 2132 bp of intron 1(lacking the 3' most 223 bp of intron 1), a PGK-neomycin resistance cassette in reverse orientation, 3' 2220 bp of Exon 3, and 4.3 Kb of sequences directly downstream of the gene, positioned upstream of a TK gene. Correct targeting of the wild-type locus with the targeting construct produced a targeted locus which lacked 7.6 Kb of the wild-type locus. The deleted region included the 3' most 223 bp of intron 1, all of exon 2, all of intron 2, and the 5' 1880 bp of exon 3 (which encompassed all of the coding region).

Generation of heterozygous Sspn$^{+/-}$ ES cells.

The targeting construct was linearized with Not 1 and introduced into $2 \times 10^7$ $R_1$ ES cells by electroporation (BioRad Gene Pusler, Hercules, CAlif.). The ES cells were maintained on feeder layers under the selective pressure of G418 and gancyclovir. Colonies surviving the selection were isolated, expanded and screened for targeting fidelity by Southern blot analysis using probe 1 (FIG. 1). Nine targeted clones were obtained from 236 analyzed. These clones were subsequently re-confirmed by Southern Blot analysis with a second probe to verify correct targeting, and additionally were probed for the neo gene to confirm a single targeting event.

Generation of chimeric mice.

Cells from two targeted clones (U104 and U202) were microinjected into C57BL/6J blastocysts and transferred into pseudopregnant recipients. Chimeric animals resulting from the microinjections were bred to C57BL/6J mice and the animals were screened for germline transmission of the mutant allele. The genotypes from these matings and all subsequent matings were determined by PCR on DNA from tail biopsies (See FIG. 1). The following primers and PCR conditions were used: SPNi1FA: ACTCCCTGGAATACA-GAGGAACT (SEQ ID NO: 1); SPNi2RA: TACAAGGG-GACAGACACTCAGAC (SEQ ID NO: 2); NEOspnKO: TTTCTCTTGATTCCCACTTTGTG (SEQ ID NO: 3). First denaturation at 94° C. for 2 min, followed by 35 cycles of 1 min at 94° C., 1 min at 55° C., 1.5 min at 72° C. Additionally, Southern analysis was periodically performed to confirm the fidelity of the PCR reaction. Analysis has been carried out on the mixed C57BL/6—129-SV/J background. All animals were housed in the animal care unit of the University of Iowa College of Medicine according to animal care guidelines.

Maintenance of mice.

Mice of all genotypes were maintained together under the same conditions. Animals were housed in three different facilities at the University of Iowa. Two of the three facilities were pathogen free facilities. Mice from all three facilities exhibited similar phenotypes. Mice were maintained under conditions standard in the art. The mice were housed in containers, approximately 20 cm wide, 30 cm long and 12 cm tall. 3–4 mice of the same sex per cage. The mice were fed a standard laboratory chow diet (NIH-31 modified mouse/rat sterilizable diet 7013) and allowed to eat at will. Mice were given chlorinated tap water and allowed to drink at will. Mice were weaned from their mothers at 3 weeks of age. A light cycle of 12 hours of light and 12 hours of darkness was used, and the mice did not receive any additional exercise other than roaming in their cages.

Antibodies.

Polyclonal antibodies against mouse sarcospan were generated by injecting New Zealand White rabbits at intramuscular and subcutaneous sites with a C-terminal sarcospan-GST fusion protein (amino acids 186 to 216 of mouse sarcospan) (Crosbie et al.,J. Cell Biol. 145: 153–165 (1999), or with an N-terminal sarcospan-GST fusion protein (amino acids 1 to 25 of mouse sarcospan: MGRKPSPRAQELPEEEARTCCGCRF (SEQ ID NO: 4). The polyclonal antibody generated against the N-terminal sarcospan-GST fusion protein is also referred to herein as R256. Affinity purification of sarcospan antibodies was accomplished using Immobilon-P (Millipore, Burlington, Mass. strips containing C-terminal or N-terminal sarcospan MBP-fusion proteins. Antibody specificity was verified for immunofluorescence and immunoblotting by competition experiments utilizing the corresponding fusion proteins and peptides synthesized to these regions. Antibodies specific for other components of the DGC were used as previously described (Duclos et al., J. Cell Biol. 142: 1461–1471 (1998).

RNA isolation and Northern Blot analysis.

Total RNA from control, heterozygous, and homozygous-null skeletal muscle, and intrascapular brown adipose tissue was extracted using RNAzol (Tel-Test, Friendswood, Tex.) according to manufacturer specifications. 20 µg of total RNA was run on a 1.25% agarose gel containing 5% formaldehyde and transferred to Hybond N membrane (Amersham Corp., Arlington Heights, Ill.). RNA was cross-linked to the membrane using a Stratagene UV cross-linker (La Jolla, Calif.). Membranes were prehybridized and hybridized using standard methods. Washes were carried out at 65° C. in 1×SSC/1% SDS followed by 0.1×SSC/0.1% SDS, which is considered to be a high stringency wash. The probe corresponded to the entire coding sequence of the sarcospan gene and also included some 3' untranslated sequences (nt 1–1256).

RT-PCR analysis for sarcospan transcript. 2 µg of total RNA from control mouse skeletal muscle and intrascapular brown adipose tissue was reverse-transcribed using 50 units reverse transcriptase (Stratagene) and an oligo (dT) primer. This CDNA was subsequently used to determine if sarcospan-specific products could be amplified from these tissues. Two sets of sarcospan-specific primers were used: N1uSPN: AACATGGGGCGCAAGCCGAG (SEQ ID NO: 5) and C2LSPN: TTAGGCCTTTGGTAGCTGGC (SEQ ID NO: 6) or L1uSPN: TTTGCCGCCCACCACTACTCCCTG (SEQ ID NO: 7) and C2LSPN. The following PCR conditions were used: 94° C. 5 min initial incubation followed by 35 cycles of 45 seconds at 94° C., 30 seconds at 60° C., and 1.5 min at 72° C. followed by a 10 minute final extension at 72° C.

Immunofluorescence and histological analysis of tissue.

Skeletal muscle from quadriceps, cardiac muscle, and smooth muscle from the small intestine was isolated from wild-type, heterozygous and sarcospan-deficient 4-week old littermate animals. Tissue was rapidly frozen in liquid nitrogen-cooled isopentane. Seven-micrometer cryosections were analyzed by immunofluorescence using antibodies as previously described (Duclos et al., J. Cell Biol. 142: 1461–1471 (1998) or by staining with hematoxylin and eosin (H&E).

Measurement of serum creatine kinase levels. Serum creatine kinase levels were quantified by using a kinetic determination of creatine kinase activity in serum obtained by blood drawn from the retro-orbital sinus. The creatine kinase assay was carried out on a Hitashi 917 instrument by the University of Iowa Department of Pathology, Chemistry laboratory.

Membrane preDarations for immunoblot analysis. KCl-washed membranes from skeletal muscle were prepared as previously described (Ohlendieck et al., J. Cell Biol. 115: 1685–1694 (1991) with the addition of two protease inhibitors, calpeptin and calpain inhibitor 1 (Duclos et al.,J. Cell Biol. 142: 1461–1471 (1998) (Calbiochem-Nova-biochem Corp., San Diego, Calif.). Total membranes from the intrascapular brown adipose tissue and epididymal white fat pads were prepared in the following manner: Tissue was dissected and snap frozen in liquid nitrogen. Frozen tissue was pulverized with a mortar and pestle in the continual presence of liquid nitrogen. The tissue was subjected to dounce homogenization in homogenization buffer (Ohlendieck et al., J. Cell Biol. 115: 1685–1694 (1991) including protease inhibitors. The samples were centrifuged at 142,400 g and the pellets were re-suspended in Buffer I including protease inhibitors (Ohlendieck et al., J. Cell Biol. 115: 1685–1694 (1991).

Immunoblot analysis of membrane preparations. KCl-washed microsomes from skeletal muscle or total membranes from white and brown heterozygote or sarcospan-deficient mice were fractionated by SDS-PAGE. 100 µg of protein per lane was fractionated by linear gradient gel electrophoresis on a 3–15% SDS-polyacrylamide gel and then transferred to nitrocellulose membranes. The nitrocellulose membrane was then immunoblotted and probed for either α-, β-, γ- δ- and ε-sarcoglycan, sarcospan, or α- and β-dystroglycan. Immunoblot analysis was performed as previously described with the exception that blots were developed using enhanced chemiluminescence (Supersignal, Pierce Chemical Co.).

Growth and Differentiation of 3T3 L1 cells. 3T3 L1 fibroblasts were cultured in DME containing 10% calf serum (Green et al., Cell 5: 19–27 (1975). Differentiation into adipocytes was induced as previously described by Frost and Lane (JBC 260: 2646–2652 (1985). Cells were used 10 days after differentiation.

Immunofluorescence analysis of 3T3 L1 cells. Immunofluorescence of undifferentiated 3T3 L1 fibroblasts and differentiated adipocytes was carried out in the following manner: Cells were plated onto coverslips in their normal growth medium. On day 4 the cells were either washed in PBS and fixed with 2% paraformaldehyde in PBS for 10 minutes, or subjected to the differentiation protocol and fixed at differentiation day 10. Fixed cells were incubated for 30 min in 0.1 M glycine in PBS, then permeablized with 0.2% Triton X-100 in PBS for 3 min. Cells were then blocked with PBS containing 10% FBS for 30 min. Primary antibody was applied to the coverslips in PBS containing 10% FBS and incubated for 12 hours at room temperature. Cells were washed thoroughly and then incubated with secondary antibody conjugated to indocarbocyanine-3 (Jackson Immunoresearch) in PBS containing 10% FBS. Cells were then washed extensively in PBS and the coverslips were mounted onto glass slides in PermaFluor mounting medium (Shandon, Pittsburgh, Pa.) and observed under a BioRad MRC-1024 laser scanning confocal microscope. Digitized images were captured under identical conditions.

Weight determination.

Age- and sex-matched wild-type, heterozygous and sarcospan-deficient mice were weighed on a scale (Whatman LabSales) and the mean weight for each genotype was reported. At least 10 animals were weighed for each data point. To compare the weights of the intrascapular brown adipose tissue and the epididymal fat pads, the tissues were carefully dissected from 10 week old wild-type (n=5) or Sarcospan-deficient (n=6) mice and weighed individually.

Screen for sarcospan expression and function.

In Vitro Expression of Sarcospan. A human sarcospan expression construct was prepared by PCR amplification of cDNA using primers containing appropriate restriction sites for subcloning into pcDNA3 (Pharmacia Biotech, Inc.). The sarcospan expression construct was engineered to encode a myc-tag at the COOH terminus. The construct was verified by direct DNA sequence analysis performed by the DNA Core Facility at the University of Iowa. CHO cells were electroporated with 10 µg of the sarcospan expression construct at 340 V, 950 µF using a BioRad electroporator. 30 hours after electroporation, cells were analyzed for protein expression by SDS-PAGE and immunoblotting with 9E10 monoclonal antibodies (anti-myc) or Rabbit 216 polyclonal antibodies (anti-human sarcospan).

Cell swelling assay. CHO cells were transiently transfected with constructs containing either green fluorescent protein (GFP) pEGFP-C3 (Clontech) and stargazer or GFP and sarcospan, by electroporation as described above. Confluent monolayers of transfected CHO cells were grown on sterile glass coverslips. The cells were rinsed with PBS (295mOsm) and placed cell-side down onto a glass slide chamber. Transfected cells were identified by green fluorescence from expression of GFP protein and transfection efficiency was estimated to be over 90%. A Bio-Rad MRC-600 laser scanning confocal was used to acquire a time series of images every 2 seconds for 5 minutes. Initial images of the cells were collected before the diluted PBS buffer (98mOsm) was introduced. Buffer exchange within the chamber was accomplished within milliseconds. The sarcospan expressing CHO cells were observed to swell three to four times more rapidly than their mock or stargazer-transfected controls when placed in a hypoosmotic solution (98mOsm). PCR amplification of sarcospan. All PCR amplifications were performed in 100 µl volumes containing 100 ng of human genomic DNA, 200 ng of each primer, 2.5 mM dNTPs, and 10 U of TAQ DNA polymerase (Boehringer Mannheim). PCR buffer for all amplifications, except amplification of exon 1, consisted of: 10 mM Tris-HCl, 1.5 mM $MgCl_2$, 50 mM KCl, pH 8.3. Thermocycling was carried out in a Hybaid Thermocycler (Omnigene) with the following cycling conditions: 1 ×92° C. for 2 min, 35 ×(94° C. for 1 min, Tm (annealing temperature) for 1 min, 72° C. for 1 min) followed by 1 ×72° C. for 10 mins. Exon 1: The Advantage-GC genomic PCR kit (Clontech) was used to amplify the GC rich region of exon 1. The PCR buffer consisted of 40 mM Tris-HCl pH 9.3, 2 mM $MgCl_2$, 85 mM KOAc, 5% dimethylsulfoxide, 0.5% Triton X-100, 1.1 mM $Mg(OAc)_2$ and 30 µl of GC Melt (Clontech). Forward primer was: 5'-GCCACGCGGCCAGCAGAGGCAGG-3' (SEQ ID NO: 8), reverse primer was: 5'-AACGCGCTTAGGCAAAACAGAC-3' (SEQ ID NO: 9), with a Tm of 57° C. The correct PCR product size was 300 bp. Exon 2: Forward primer was: 5'-GAACGCACAACGTACCCTGATAAC-3' (SEQ ID NO: 10), Reverse primer was: 5'-TGTGATGATAAAAGAGAAAGAACA-3' (SEQ ID NO: 11). The Tm was 50° C. and the correct resulting PCR product was 200 bp. Exon 3: Forward primer was: 5'-GGCAAATCATCATCCAATGTTCT-3' (SEQ ID NO: 12), reverse primer was: 5'-TGTGCTACTTTCTCTCGCAACT-3' (SEQ ID NO: 13), with a Tm of 50° C. The correct PCR product size was 500 bp.

Upon amplification, the PCR products were purified using a Quiquick PCR purification spin column (Quiagen). PCR products (2.5 ng/100 bp) were individually sequenced with their respective forward and reverse primers. DNA sequencing reactions were performed using the dye terminator cycle sequencing chemistry with AmpliTaq DNA polymerase, FS enzyme (PE Applied Biosystems, Foster City, Calif.). The reactions were run on and analyzed with an Applied Biosystems Model 373A stretch fluorescent automated sequencer at the University of Iowa DNA facility.

Human sarcospan adenovirus. Human sarcospan CDNA (Genbank accession AF016028) was subcloned into pAd5CMVK-NpA shuttle vector using BamHI and XbaI restriction sites. The sarcospan cDNA was engineered to contain a myc tag at the C-terminus. The shuttle vector was sequenced to verify the insertion of the sarcospan cDNA and then incorporated into an adenovirus vector through standard methods of homologous recombination with AdS backbone dl309 by the University of Iowa Gene Transfer Vector Core. Recombinant viruses were purified using established methods (Graham and van der Eb, *Virology* 52: 456–467 (1978); Davidson et al., *Exp. Neurol* 125: 258–267 (1994). Lysates from tsa-201 infected cells were collected and tested for the expression of sarcospan protein using 9E10 monoclonal antibody (anti-myc) as well as Rabbit 216 antibody (anti-human sarcospan). Recombinant virus was plaque purified, amplified, and isolated by CsCl gradient centrifugation.

Identification of polymorphism in exon 3 by restriction digest.

Exon 3 was amplified from human genomic DNA, as described above. 30 µl of the PCR product was digested individually with Hga I (4 U) and Mae II (3 U) in the buffers provided by the manufacturer (New England Biolabs) in a final volume of 50 µl. Restriction digests were performed for 1 hr at 37° C. and 50° C. for Hga I and Mae II, respectively. Cleavage of the normal and polymorphic exon 3 PCR products with Hga I resulted in PCR products of 250 bp and 450 bp, respectively. Mae II did not digest the normal exon 3 PCR product (500 bp), but did cleave the polymorphic product into two fragments of 260 and 240 bp.

SEQUENCE LISTING

<160> NUMBER OF SEQ ID NOS: 13

```
<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 1
actccctgga atacagagga act                                              23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 2
tacaagggga cagacactca gac                                              23

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 3
tttctcttga ttcccacttt gt                                               22

<210> SEQ ID NO 4
<211> LENGTH: 25
<212> TYPE: PRT
<213> ORGANISM: Artificial Sequence
<220> FEATURE:
<223> OTHER INFORMATION: Description of Artificial Sequence: Antigenic
      fragment of mouse sarcospan protein

<400> SEQUENCE: 4

Met Gly Arg Lys Pro Ser Pro Arg Ala Gln Glu Leu Pro Glu Glu Glu
 1               5                  10                  15

Ala Arg Thr Cys Cys Gly Cys Arg Phe
            20                  25

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 5
aacatggggc gcaagccgag                                                  20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: PCR primer

<400> SEQUENCE: 6
ttaggccttt ggtagctggc                                                  20

<210> SEQ ID NO 7
```

```
<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: PCR primer

<400> SEQUENCE: 7
tttgccgccc accactactc cctg                                          24

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 8
gccacgcggc cagcagaggc agg                                           23

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 9
aacgcgctta ggcaaaacag ac                                            22

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: PCR primer

<400> SEQUENCE: 10
gaacgcacaa cgtaccctga taac                                          24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: PCR primer

<400> SEQUENCE: 11
tgtgatgata aaagagaaag aaca                                          24

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 12
ggcaaatcat catccaatgt tct                                           23

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: PCR primer

<400> SEQUENCE: 13
```

-continued tgtgctactt tctctcgcaa ct                                        22

What is claimed is:

1. A transgenic knockout mouse whose genome comprises a homozygous disruption in its endogenous sarcospan gene, wherein said homozygous disruption prevents the expression of a functional sarcospan protein in cells of the mouse, and wherein said homozygous disruption results in said transgenic knockout mouse exhibiting from 1.4 to 6.8 fold larger epididymal fat pad deposits as compared to the epididymal fat pad deposits of a wild type mouse.

2. The transgenic knockout mouse of claim 1, wherein said transgenic knockout mouse has from 1.5 to 2.9 fold larger intrascapular brown adipose tissue deposits as compared to the intrascapular brown adipose deposits of a wild-type mouse.

3. The transgenic knockout mouse of claim 1, wherein said transgenic knockout mouse weighs 15% to 20% more on average than a wild type mouse.

4. The transgenic knockout mouse of claim 1, wherein said homozygous disruption results from deletion of a portion of the endogenous sarcospan gene.

5. The transgenic knockout mouse of claim 4, wherein the deleted portion of the endogenous sarcospan gene is replaced with a PGK-neomycin resistance cassette.

6. A cell isolated from the transgenic knockout mouse of claim 4, wherein the genome of said cell comprises a homozygous disruption in its endogenous sarcospan gene, and wherein said homozygous disruption prevents the expression of a functional sarcospan protein in said cell.

7. A cell derived from the transgenic knockout mouse of claim 4, wherein the genome of said cell comprises a homozygous disruption in its endogenous sarcospan gene, and wherein said homozygous disruption results from deletion of a portion of the endogenous sarcospan gene.

8. A cells derived from the transgenic knockout mouse of claim 5, wherein the genome of said cell comprises a homozygous disruption in its endogenous sarcospan gene, and wherein said homozygous disruption results from deletion of a portion of the endogenous sarcospan gene and the deleted portion of the endogenous sarcospan gene is replaced with a PGK-neomycin resistance cassette.

9. A method for identifying a therapeutic agent for the treatment of an individual diagnosed with a metabolic disorder associated with a reduction or loss of expression of wild-type sarcospan in the individual, comprising:

a) providing a transgenic knockout mouse whose genome comprises a homozygous disruption in its endogenous sarcospan gene, wherein said homozygous disruption prevents the expression of a functional sarcospan protein in cells of the mouse, wherein said homozygous disruption results in said transgenic knockout mouse exhibiting symptoms of a metabolic disorder selected from the group consisting of: larger epididymal fat deposits as compared to epididymal fat deposits of a wild-type mouse, larger intrascapular brown adipose tissue deposits as compared to the intrascapular brown adipose tissue deposits of a wild-type mouse, and increased body weight as compared to the body weight of a wild-type mouse;

b) administering a candidate therapeutic agent to the transgenic knockout mouse of step a); and c) assaying the therapeutic effects of the candidate therapeutic agent by comparing the symptoms of the metabolic disorder in the transgenic knockout mouse which has received the candidate agent as in step b) with the symptoms of the metabolic disorder of a transgenic knockout mouse of step a) which has not received the candidate therapeutic agent, wherein amelioration of one or more of the symptoms of the metabolic disorder in the transgenic knockout mouse of step b) is an indication of the therapeutic effect of the candidate therapeutic agent.

10. A method for identifying an agent for reduction of weight gain in an individual wherein said weight gain is associated with a reduction or loss of expression of wild-type sarcospan in the individual, comprising:

a) providing a transgenic knockout mouse whose genome comprises a homozygous disruption in its endogenous sarcospan gene, wherein said homozygous disruption prevents the expression of a functional sarcospan protein in cells of the mouse, wherein said homozygous disruption results in said transgenic knockout mouse exhibiting symptoms of a metabolic disorder selected from the group consisting of: larger epididymal fat deposits as compared to epididymal fat deposits of a wild-type mouse, larger intrascapular brown adipose tissue deposits as compared to the intrascapular brown adipose tissue deposits of a wild-type mouse, and increased body weight as compared to the body weight of a wild-type mouse;

b) administering a candidate agent to the transgenic knockout mouse of step a); and c) assaying the effects of the candidate agent by comparing the fat pad or adipose deposits of the transgenic knockout mouse which has received the candidate agent as in step b) with the fat pad or adipose deposits of a transgenic knockout mouse of step a) which has received the candidate agent, wherein a reduction in the fat pad or adipose deposits in the transgenic knockout mouse of step b) is an indication that the agent has a reduction of weight gain effect in the individual.

11. The method of claim 9, wherein the metabolic disorder produces an increase in the fat pad or adipose deposits of the individual, and the therapeutic effect is a decrease in the fat pad or adipose deposits of said transgenic knockout mouse.

* * * * *

UNITED STATES PATENT AND TRADEMARK OFFICE
CERTIFICATE OF CORRECTION

PATENT NO. : 6,207,878 B1
DATED : March 27, 2001
INVENTOR(S) : Campbell et al.

It is certified that error appears in the above-identified patent and that said Letters Patent is hereby corrected as shown below:

Claim 6,
Line 2, delete "claim 4" and substitute therefor -- claim 1 --.

Claim 8,
Line 1, delete "cells" and substitute therefor -- cell --.

Signed and Sealed this

Eighteenth Day of December, 2001

*Attest:*

*Attesting Officer*

JAMES E. ROGAN
*Director of the United States Patent and Trademark Office*